United States Patent [19]

Tripier

[11] Patent Number: 4,668,662

[45] Date of Patent: May 26, 1987

[54] POLYPEPTIDES WITH AN ANTICOAGULANT ACTION, A PROCESS TO PREPARE OR OBTAIN THEM, THEIR USE AND AGENTS CONTAINING THEM

[75] Inventor: Dominique Tripier, Eppstein, Fed. Rep. of Germany

[73] Assignee: Hoechst Aktiengesellschaft, Fed. Rep. of Germany

[21] Appl. No.: 724,332

[22] Filed: Apr. 17, 1985

[30] Foreign Application Priority Data

Apr. 18, 1984 [DE] Fed. Rep. of Germany ....... 3414593
Oct. 19, 1984 [DE] Fed. Rep. of Germany ....... 3438296

[51] Int. Cl.$^4$ .......................... A61K 37/43; C07K 7/10
[52] U.S. Cl. .................................. 514/12; 530/324
[58] Field of Search ................... 260/112.5 R; 514/12; 530/324

[56] References Cited

PUBLICATIONS

Biochimica et Biophysics Acta 310 (1973) 416–417.
Febs 1104 165, No. 2, (1984) 180–184.
Biochim. Biophys. Acta, 93 (1964) 40–44.
Bull. Soc. Chim. Biol. (1963) 45, 55–67.
Hirudin (The Merck Index, 9th Ed. (1976) p. 4593.

*Primary Examiner*—Delbert R. Phillips
*Attorney, Agent, or Firm*—Finnegan, Henderson, Farabow, Garrett & Dunner

[57] ABSTRACT

The invention relates to polypeptides of the formula I

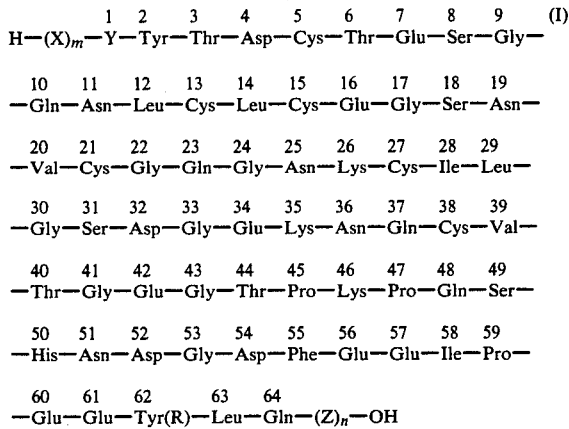

in which m denotes 0–50, n denotes 0–100 and R denotes the phenolic hydrogen or a phenol ester group, X represents identical or different residues of naturally occurring α-amino acids, Y denotes Val, Ile, Thr, Leu or Phe, and Z represents identical or different residues of naturally occurring α-amino acids, and in which the Cys residues are linked pairwise via disulfide bridges, to a process for preparing or obtaining them and to agents containing them.

5 Claims, No Drawings

POLYPEPTIDES WITH AN ANTICOAGULANT ACTION, A PROCESS TO PREPARE OR OBTAIN THEM, THEIR USE AND AGENTS CONTAINING THEM

Anticoagulants are used in the prophylaxis and therapy of thromboembolic processes; their main area of use in this context is for venous thromboembolisms, in particular. In addition, anticoagulants are required for the preparation of stored blood. Derivatives of 4-hydroxycoumarin or of 1,4-indanedione, which are, for example, used for this purpose, have a number of disadvantages, in spite of substantial optimization (cf., for example, Mutschler, Arzneimittelwirkungen (Drug Actions), 4th edition, Stuttgart 1981, pages 375 et seq.).

Thus, it is desirable to have available, especially in human medicine, anticoagulants which have low toxicity and few side effects and which impose no stress by their metabolism on the diseased organism.

Apart from endogenous plasmatic inhibitors, such as antithrombin III, many other proteins also have an anticoagulant action, such as, for example, the Kunitz inhibitor which is obtained from soybeans. This inhibitor blocks the coagulation cascade by inhibition of activated factor Xa, but the specificity of the inhibitor is so low that many side effects occur: inhibition of plasma kallikrein, of plasmin and of trypsin, so that therapeutic administrations are ruled out. Other active compounds, such as the Ascaris or the Kazals inhibitor, have been unable to achieve any significance, because of lack of specificity, either.

Hirudin (The Merck Index, 9th edition, Rahway 1976, page 618; Pharmazie 36 [1981] No. 10), a polypeptide which is obtained from Hirudo medicinalis, in contrast shows a specific antithrombin activity (cf., for example, Markwardt, Blutgerinnungshemmende Wirkstoffe aus blutsaugenden Tieren (Anticoagulant Active Compounds from Blood-sucking Animals), Jena 1963). The elaborate process for its isolation and purification has hitherto militated against its use in practice.

It has now been found, surprisingly, that a highly active polypeptide of the formula II in which R denotes hydrogen or SO₃H, can be isolated from leeches.

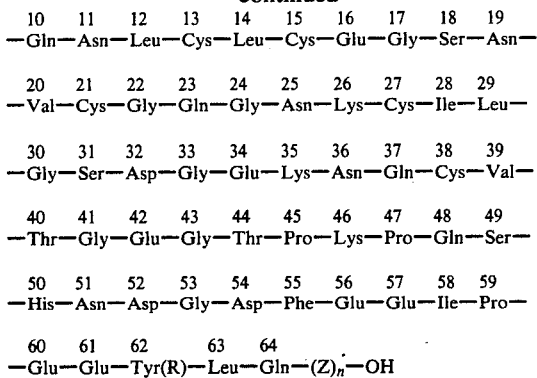

This invention thus relates to polypeptides of the formula I

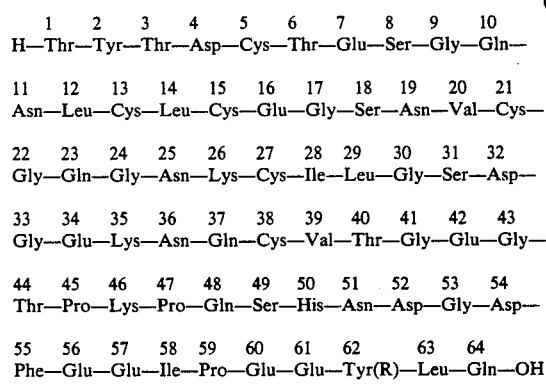

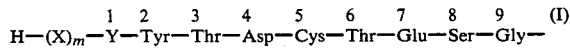

in which
m denotes 0–50,
n denotes 0–100, and
R denotes the phenolic hydrogen or a phenol ester group,
X represents identical or different residues of naturally occurring α-amino acids,
Y denotes Val, Ile, Thr, Leu or Phe, and
Z represents identical or different residues of naturally occurring α-amino acids, and
in which the 6 Cys residues at positions 5, 13, 15, 21, 27 and 38 are linked pairwise via disulfide bridges, and to their physiologically tolerated salts, an exception being made of the polypeptide of the formula I in which H—(X)$_m$—Y represents H-Val-Val, and n denotes 0.

Naturally occurring α-amino acids are, in particular, Gly, Ala, Ser, Thr, Val, Leu, Ile, Asp, Asn, Glu, Gln, Cys, Met, Arg, Lys, Hyl, Orn, Cit, Tyr, Phe, Trp, His, Pro and Hyp.

R preferably denotes hydrogen, SO₃H or PO₃H₂, Y preferably denotes Thr, and m and n each preferably denote 0.

Preferred meanings of both X and Z are Ala, Ile, Val, Tyr or Phe.

Particularly suitable salts are alkali metal and alkaline earth metal salts, salts with physiologically tolerated amines and salts with physiologically tolerated acids, such as HCl, H₂SO₄, maleic acid or acetic acid.

The invention also relates to biologically active peptide cleavage products which are obtainable by chemical or enzymatic cleavage of these polypeptides.

The invention furthermore relates to a process for obtaining a purified polypeptide of the abovementioned formula, which comprises isolation of the polypeptide from worms of the phylum Annelida using a combination of extraction methods, precipitation methods, membrane filtration and/or chromatographic processes, and conversion of the resulting peptide, where appropriate, into its physiologically tolerated salts.

The polypeptide is preferably obtained from the cervical glands of worms of the class Hirudinea, in particular from those of the order Gnathobdellida. The genera Hirudo and Haemodipsa are preferred. The genus Hirudo is particularly preferred, and from this, in particular, Hirudo medicinalis. Apart from the cervical glands of the leech, it is also possible to use the front parts of its body or the whole leech.

A process for obtaining a crude extract from leeches is described in Enzymology, Volume 5 "Hirudin as an Inhibitor of Thrombin". A process for the purification of Hirudin is disclosed in Bull. Soc. Chim. Biol. 45 [1963] 55.

In the process according to the invention, a combination of precipitation methods and gel permeation chromatography, or ultrafiltration, and high-resolution partition chromatography on "reverse-phase" material and chromatography on silica gel or alumina has proved particularly useful. However, depending on the nature of the crude extract, it is also possible for other chromatographic processes to be applied advantageously (where appropriate also in combination with the above-mentioned process), such as, for example, cation or anion exchange chromatography, or chromatography on non-specific absorbents, in particular hydroxyapatite.

In order to obtain a crude extract which is suitable for chromatography, for example, the head parts of the leech can be comminuted in the frozen state and extracted using an aqueous buffer solution (for example phosphate buffer). The insoluble material is removed by, for example, brief centrifugation or by filtration through gauze, and the polypeptide is removed from the extract thus obtained and is isolated. It is advantageous to heat this extract rapidly to 70° to 90° C. because this leads to the denaturation and precipitation of the major amount of the proteolytic enzymes which can then be removed by, for example, centrifugation. The protein fraction which contains the peptide according to the invention is isolated from the extract by, for example, precipitation in such a manner that the extract is added to an organic solvent which is miscible with water. For example, acetone can be used in a quantity which is a multiple of the volume of the extract, preferably about 10 times the quantity, the precipitation being carried out in the cold, normally at 0 to −40° C., preferably at about −20° C.

Proteins with high molecular weights can be removed from this crude extract by, for example, ultrafiltration or by gel permeation chromatography. The ultrafiltration of larger batches can be carried out in, for example, two stages: in the first stage, a capillary membrane with an exclusion limit of 500,000 Dalton is used and then, in the second stage, a flat membrane with an exclusion limit of 10,000 Dalton is used. By use of the capillary membrane, rapid removal of high molecular weight material which would impede the flow through the selectively operating flat membrane is achieved. It is also possible with small amounts to dispense with the first stage of ultrafiltration.

Another possibility of carrying out the precipitation is to add salts such as, for example, ammonium sulfate. The precipitation achieves a certain selectivity by control of the pH. The peptide according to the invention, which has an isoelectric point of 3.9, can be precipitated by addition of ammonium sulfate up to a concentration of about 50% in the pH range between 3 and 5, preferably about 4, a large number of concomitant proteins remaining in solution during this. This precipitation is likewise carried out while cooling, at about −5° to +15° C., preferably between 0° and +4° C.

The material thus obtained on the basis of the method used hitherto still comprises a mixture of polypeptides. A preferred process for obtaining the inhibitor of the formula II with R=H or SO$_3$H comprises the fractionation of the crude extract by one, or several, high-resolution chromatographic systems. This fraction can in turn be resolved into individual components in a second high-resolution chromatographic system in order thus to isolate the inhibitor of the formula II.

Processes as are disclosed in, for example, European Pat. No. A-82359 have proved advantageous as the first chromatographic stage for obtaining these inhibitors. This entails the mixtures of proteins being separated on conventional silica gel of suitable particle size or on ready-packed silica gel columns (such as, for example, the Lobar ® column) using a buffer system.

The sample can be applied to the column in the form of a preequilibrated column. However, it is also possible to apply the mixture of substances to the dry column without adverse effects.

A ratio between the mixture of proteins and the absorbents which is between 1:50 and 1:200 has proved to be advantageous.

The elution can be carried out with a buffer composed of chloroform, methanol, glacial acetic acid, water and triethylamine. It is also possible to use other buffer solutions for this purpose, such as, for example, 70% ethanol, 30% tris buffer (0.05 M, pH 8.0).

The last purification step comprises chromatographic separation on "reverse-phase" material. Due to the high resolution of HPLC technology, cf., for example, "High Performance Liquid Chromatography - Advances and Perspectives", Volume 3, Csaba Horvath, Academic Press, 1983, pages 50–83, or "Methods of Enzymology", Volume 91, pages 137–190 and 352–359, 1983, it is possible to separate the inhibitors of the formula II from concomitant proteins and to prepare them pure.

Derivatized silica gels of suitable particle size (for example between 3 and 20 μm) have proved to be advantageous for the stationary phase. Apart from the widely used octadecylsilane radicals, a large number of other silane radicals or their mixtures are suitable for the derivatization of the silica gel, such as silane radicals having lower alkyl, phenylalkyl- or amino-substituted alkyl, the latter allowing a certain combination of ion exchange and "reverse-phase" chromatography. It is possible to use, for example, separating columns 5 to 25 cm in length and 3 to 10 mm in diameter. Suitable buffered eluting agents are all secondary or tertiary mixtures of water and organic solvents of suitable lipophilicity, such as, for example, lower alcohols, ketones, nitriles, ethers, acids, amines, glycol ethers, amides and their derivatives. Organic and inorganic salts or other types of additives can be used as the buffer substance. The elution is preferably carried out at a pH between 2 and 8.

The use of volatile buffer substances, such as ammonium acetate or ammonium bicarbonate, allows the inhibitors to be obtained from the eluate by simply freeze-drying.

The polypeptide of the formula II, according to the invention, is colorless, soluble in water and in aqueous buffers, proves to be homogeneous on polyacrylamide electrophoresis and has an isoelectric point of 3.9 (determined by isoelectric focusing). When the amino acid composition is determined by the method of Moore and Stein (Methods of Enzymology, Volume VI, 819–831, edited by Rolovick and Kaplan, Academic Press, New York, London, 1963), the following figures are found: 9 aspartic acid, 5 threonine, 4 serine, 13 glutamic acid, 3 proline, 9 glycine, 2 valine, 6 cystein, 2 isoleucine, 4 leucine, 2 tyrosine, 1 phenylalanine, 3 lysine and 1 histidine.

The invention also relates to a process for the preparation of a polypeptide of the abovementioned formula I, which comprises (a) preparing it in a manner known per se by solid-phase synthesis or (b) for the preparation of a polypeptide in which n is 0, I. subjecting hirudin to two Edman degradations, II. reacting the peptide which is obtained thus with an active ester of an amino acid or of a peptide of the formula U—$(X)_m$—Y—OH, in which m, X and Y are as defined above, and U represents an acid- or base-labile urethane protective group, III. eliminating the phenylthiocarbamoyl group on the $\epsilon$-amino group of Lys using hydrazine and IV. eliminating the urethane protective group U using an acid or base, and, where appropriate, the polypeptide obtained in (a) or (b) is converted into its physiologically tolerated salt.

In solid-phase synthesis (cf. in this context Atherton, Sheppard, Perspectives in Peptide Chemistry, Karger Basel 1981, pages 101–117), as a rule it is possible to dispense with an OH protective group for Thr.

The synthesis of the polypeptide of the formula I is carried out, for example, stepwise on hydroxymethylated polystyrene resin. The polystyrene is crosslinked with, for example, 1% divinylbenzene. It is usually in the form of small beads.

The amino acids are used with N-terminal protection. The first N-protected amino acid is attached to the support by ester formation. After removal of the amino protective group, the next N-protected amino acid is linked on by use of a coupling reagent such as dicyclohexylcarbodiimide. Deprotection and addition of further amino acids is continued until the desired sequence is reached.

The choice of protective groups depends on the amino acids and the coupling methods.

Examples of suitable amino protective groups are the known urethane protective groups such as benzyloxycarbonyl(Z), p-methoxycarbobenzoxy, p-nitrocarbobenzoxy, t-butyloxycarbonyl(Boc), Fmoc and the like.

The Boc group is preferred since it can be eliminated with relatively mild acids (for example trifluoroacetic acid or HCl in organic solvents).

Threonine can be blocked as the benzyl ether, and the $\epsilon$-amino group in lysine can be blocked as the Z derivative. Both these protective groups are very substantially resistant to the reagents for elimination of the Boc group, and they can be removed by hydrogenolysis using a hydrogenation catalyst (Pd/active charcoal) or with, for example, sodium in liquid ammonia.

The protected peptide can be removed from the resin using, for example, hydrazine. This results in the hydrazide which can be converted into the free carboxylic acid using, for example, N-bromosuccinimide by the method in Int. J. Pept. Prot. Research 17 [1981] 6–11. Where necessary, the disulfide bridges must be closed by oxidation (cf., König, Geiger, Perspectives in Peptide Chemistry, Karger Basel, pages 31–44).

In process variant b), hirudin is subjected to two Edman degradations by reacting this polypeptide with an isothiocyanate, preferably phenylisothiocyanate, in a suitable buffer solution such as pyridine/water or dioxane/water, where appropriate with the addition of a base such as NaOH or triethylamine, preferably at about 40° C. and a pH of 8–9. The N-terminal valine is eliminated as phenylthiazolinone by treatment with an acid (for example 3N HCl at room temperature followed by heating to 40° C). This reaction sequence is repeated to cleave the second valine at the N-terminal end.

The de-(Val)$_2$-hirudin derivative obtained in this manner is reacted with an active ester of an amino acid or of a peptide of the formula U—$(X)_m$—Y—OH. Examples of suitable esters are the p-nitrophenyl, cyanomethyl, N-hydroxyphthalimido or, in particular, the N-hydroxysuccinimido ester. Suitable urethane protective groups U are those which can be eliminated by acid or alkali, such as, for example, Boc or Msc. Where necessary, it is also possible to protect temporarily by suitable protective groups any groups present in the side chains of X and Y.

The protected precursor of the polypeptide of the formula I (n=0) which is obtained in this manner is treated with hydrazine hydrate in a suitable solvent, such as a lower alcohol or its mixture with water, to eliminate the phenylthiocarbamoyl group on lysine.

The remaining protective group(s) on this polypeptide are now also eliminated in a suitable manner (Boc with, for example, trifluoroacetic acid, and Msc with a base), and the polypeptide of the formula I, according to the invention, is thus obtained.

The polypeptides according to the invention are specific stoichiometric inhibitors of thrombin. Quantitative measurement of the inhibition of thrombin by the inhibitors according to the invention has shown that the inhibitor-thrombin complex undergoes virtually no dissociation. It is possible using this method of measurement to determine the activity, and hence the degree of purity, of the polypeptides according to the invention during working up and purification. The polypeptide of the abovementioned formula II which has been purified in this way can show thrombin inhibition of more than 10,000 ATU/mg by this method and thus exceed that of the conventional hirudin.

Thus the invention also relates to the use of polypeptides of the formula I in which m, n, R, X, Y and Z have the abovementioned meaning and, furthermore, Y can also denote a chemical bond as anticoagulants for administration for the treatment of thromboembolic processes and to their use as diagnostic aids and reagents.

The invention also relates to agents which contain a polypeptide of the formula I in a pharmaceutically acceptable vehicle, and to a process for their preparation which comprises converting them into a suitable administration form. The compounds according to the invention can be administered parenterally or topically in an appropriate pharmaceutical preparation.

For subcutaneous or intravenous administration, the active compounds or their physiologically tolerated salts are converted into a solution, suspension or emulsion, if desired using the substances customary for this purpose, such as solubilizers, emulsifiers, agents for isotonicity, preservatives or other auxiliaries. Examples of suitable solvents for the new active compounds and the corresponding physiologically tolerated salts are: water, physiological saline solutions or alcohols, for example ethanol, propanediol or glycerol, as well as sugar solutions, such as glucose or mannitol solutions, or a mixture of the various solvents mentioned.

The topical vehicles can be organic or inorganic compounds. Typical vehicles used in pharmacy are aqueous solutions which are, for example, buffer systems or isotonic mixtures of water and solvents which are miscible with water, such as, for example, alcohols or aryl alcohols, oils, polyalkylene glycols, ethylcellulose, carboxymethylcellulose, polyvinylpyrrolidone or isopropylmyristate. Examples of suitable buffer substances are sodium borate, sodium phosphate, sodium acetate or gluconate buffer. The topical administration form can also contain non-toxic auxiliaries such as, for example, emulsifying preservatives, wetting agents such as, for example, polyethylene glycols, and antibacterial compounds.

EXAMPLE 1

Determination of the inhibitor concentration by thrombin titration

200 μl of sodium bicarbonate solution (pH =7, 0.05 M) are added to 10 to 100 μl of the inhibitor solution in which the protein content has previously been determined. 0.1 ml of fibrinogen solution (0.5 to 1%) or diluted citrated plasma is added; an aliquot (50–100 μl) of the thrombin solution (about 100 NIH units per ml) is added at regular intervals while stirring at room temperature. The end point which can be used for semi-quantitative work is coagulation of the fluid within the selected time interval, and that for quantitative determination can be found by turbidimetric measurement at 546 nm.

EXAMPLE 2

Free-living leeches (not bred animals) of the species Hirudo medicinalis, which had been collected in Germany, are used.

About 150–200 g of frozen front parts of leeches are homogenized in a mixer with 2 l of ice-cold 0.09% sodium chloride solution and 10 ml of octanol within 3 minutes. After centrifugation at 0° C. and 10,000 rpm for 30 minutes, the supernatant is further clarified by filtration through 2 layers of gauze and the filtrate is then heated to 80° C. within 15 minutes, with stirring. The resulting precipitate is removed by filtration through 4 layers of gauze. The filtrate is rapidly cooled to 4° C. by stirring in an ice bath, and is added to 7.5 l of precooled acetone ($-20°$ C). Another precipitate is produced and, after 5 minutes, this is filtered off through a glass filter with suction, and is washed with 1 l of cold acetone ($-20°$ C). After drying in vacuo, 520 mg of pale yellowish powder with a protein content of 62% (determined by the Lowry method) are produced. The antithrombin activity is about 400 units per mg.

EXAMPLE 3

520 mg of powder from Example 1 are dissolved in 75 ml of water, then the pH is adjusted to 8.0 with 5 N ammonia, and the mixture is stirred at 0°–4° C. for 1 hour. The insoluble fraction is centrifuged down within 30 minutes using a cup centrifuge at 5,000 rpm. After adjustment of the protein content to 25 mg/ml (Lowry) by addition of water, 35 ml of saturated ammonium sulfate solution are added to the solution which is then stirred at 4° C. for 1 hour. The first precipitate is rapidly removed by centrifugation (5,000 rpm/30 minutes). About 26 g of ammonium sulfate are again dissolved in the solution, and the pH is adjusted to pH 4 with glacial acetic acid. After standing for 5 hours, the entire suspension is centrifuged and the resulting moist precipitate is further processed as follows.

EXAMPLE 4

The moist precipitate obtained in Example 3 is dissolved in 200 ml of 0.1 M ammonium bicarbonate solution of pH 8, and is subjected to ultrafiltration in a 250 ml Amicon ® cell with a 5PM 10 flat membrane (exclusion limit 10,000 Dalton). The solution is concentrated to about 40 ml during this, towards the end replenishment with 150 ml of 0.1 M ammonium bicarbonate solution of pH 8.0 being carried out twice. Freeze-drying of the residue results in about 350 mg of material with a protein content of 89%.

A C column (Merck) is packed with silica gel 50 μm 100 Å (Grace) while agitating (vibromixer). 500 mg of extract from Example 4 are dissolved in 5 ml of a mixture of chloroform, methanol, glacial acetic acid, water and triethylamine in the ratio by volume 1,200:1,200:4:400:12, with 0.2% ammonium acetate, and applied to the column. The column is eluted with the same mixture at a rate of about 4 ml/min, and 5–10 ml fractions are taken. After the eluate has been dried, the fractions containing inhibitor are dissolved in sodium bicarbonate (pH=7.0, 0.5 M) and collected. The yield is about 50 mg and the activity is 4,000 ATU/mg.

EXAMPLE 6

20 mg of inhibitor from Example 3 are dissolved in 200 μl of water of pH 2.16 (adjusted with trifluoroacetic acid +5% acetonitrile) and injected onto a steel column packed with octadecylsilane-silica gel (5 μm) (Shandon-®ODS). The column is eluted with a gradient at a maximum of 2%/minute between the starting buffer (water, pH=2.16, +5% acetonitrile) and the final buffer (acetonitrile/water, pH=2.16, 80/20). The fractions are collected singly. After drying, the inhibitor of the formula II (R=H or SO$_3$H), according to the invention, has a specific activity which is consistent with the stoichiometry of a 1:1 complex with thrombin.

I claim:

1. A polypeptide of the formula I

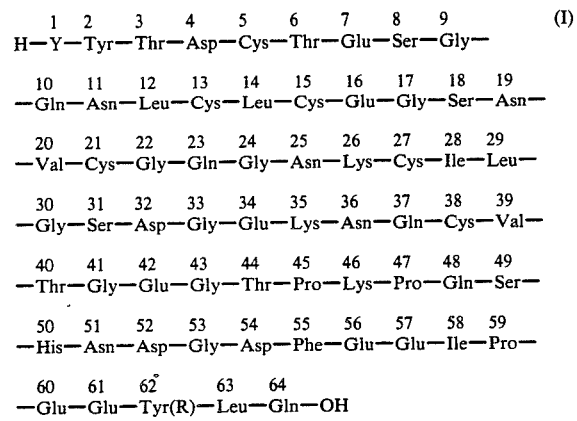

wherein
R denotes the phenolic hydrogen or a phenol ester group, and Y denotes Val, Ile, Thr, Leu or Phe, and in which the six Cys residues at positions 5, 13, 15, 21, 27 and 38 are linked pairwise via disulfide bridges, and its physiologically tolerated salts.

2. The polypeptide of claim 1, wherein R denotes hydrogen, SO$_3$H or PO$_3$H$_2$.

3. The polypeptide of claim 1 wherein Y denotes Thr.

4. A pharmaceutical agent for treating thromboembolic process containing a polypeptide of the formula I as claimed in claim 1, or its physiologically tolerated salt, in an amount which is effective for anticoagulation, and a pharmaceutically acceptable vehicle.

5. A method for the treatment of thromboembolic processes comprising administering an effective amount of polypeptide as claimed in claim 1 or a pharmaceutically acceptable salt thereof.

* * * * *